United States Patent
Aven et al.

(10) Patent No.: US 11,819,549 B2
(45) Date of Patent: Nov. 21, 2023

(54) PHARMACEUTICAL FORMULATION COMPRISING CICLESONIDE

(71) Applicant: Boehringer Ingelheim Vetmedica GmbH, Ingelheim am Rhein (DE)

(72) Inventors: Michael Aven, Mainz (DE); Benjamin Franzmann, Merxheim (DE); Matthias Hausmann, Rees (DE)

( * ) Notice: Subject to any disclaimer, the term of this patent is extended or adjusted under 35 U.S.C. 154(b) by 377 days.

(21) Appl. No.: 17/132,038

(22) Filed: Dec. 23, 2020

(65) Prior Publication Data

US 2021/0106685 A1 Apr. 15, 2021

Related U.S. Application Data

(62) Division of application No. 14/132,578, filed on Dec. 18, 2013, now Pat. No. 10,925,964.

(30) Foreign Application Priority Data

Dec. 21, 2012 (EP) .................................... 12199302
Oct. 25, 2013 (EP) .................................... 13190393

(51) Int. Cl.
*A61K 47/02* (2006.01)
*A61K 9/00* (2006.01)
*A61K 9/08* (2006.01)
*A61P 11/00* (2006.01)
*A61K 31/58* (2006.01)
*A61K 47/10* (2017.01)

(52) U.S. Cl.
CPC ............ *A61K 47/02* (2013.01); *A61K 9/0073* (2013.01); *A61K 9/08* (2013.01); *A61K 31/58* (2013.01); *A61K 47/10* (2013.01); *A61P 11/00* (2018.01)

(58) Field of Classification Search
CPC combination set(s) only.
See application file for complete search history.

(56) References Cited

U.S. PATENT DOCUMENTS

| | | |
|---|---|---|
| 5,823,179 A | 10/1998 | Grychowski et al. |
| 5,954,049 A | 9/1999 | Foley et al. |
| 6,264,923 B1 | 7/2001 | Oliver et al. |
| 6,706,726 B2 | 3/2004 | Meissner et al. |
| 7,244,742 B2 | 7/2007 | Pieper et al. |
| 2003/0234015 A1 | 12/2003 | Bruce et al. |
| 2004/0266869 A1 | 12/2004 | Montague et al. |
| 2006/0110329 A1 | 5/2006 | Pieper et al. |
| 2006/0069073 A1 | 6/2006 | Pieper et al. |
| 2006/0293293 A1 | 12/2006 | Muller et al. |
| 2007/0025923 A1 | 2/2007 | Wurst et al. |
| 2007/0117783 A1 | 5/2007 | Brueck-Scheffler |
| 2007/0134165 A1 | 6/2007 | Wurst et al. |
| 2008/0041369 A1 | 2/2008 | Radau et al. |
| 2008/0041370 A1 | 2/2008 | Radau et al. |
| 2012/0039817 A1 | 2/2012 | Verhring et al. |
| 2012/0058980 A1 | 3/2012 | Radau et al. |
| 2014/0116427 A1 | 5/2014 | Pevler et al. |
| 2014/0179650 A1 | 6/2014 | Aven et al. |
| 2014/0179651 A1 | 6/2014 | Albrecht et al. |
| 2015/0053202 A1 | 2/2015 | Knell et al. |
| 2015/0053203 A1 | 2/2015 | Knell et al. |
| 2015/0202148 A1 | 7/2015 | Cifter et al. |
| 2015/0202297 A1 | 7/2015 | Cifter et al. |
| 2015/0313918 A1 | 11/2015 | Albrecht et al. |
| 2015/0366855 A1 | 12/2015 | Albrecht et al. |
| 2017/0007593 A1 | 1/2017 | Albrecht et al. |
| 2017/0079988 A1 | 3/2017 | Albrecht et al. |

FOREIGN PATENT DOCUMENTS

| | | |
|---|---|---|
| CA | 2495454 A1 | 3/2004 |
| WO | 1997012687 A1 | 4/1997 |
| WO | 2002032899 A1 | 4/2002 |
| WO | 2004022058 A1 | 3/2004 |
| WO | 2004023984 A1 | 3/2004 |
| WO | 2006056527 A1 | 6/2006 |
| WO | 2010149280 A1 | 12/2010 |
| WO | 2014096115 A1 | 6/2014 |
| WO | 2015193213 A1 | 12/2015 |

OTHER PUBLICATIONS

Belvisi et al., "Preclinical Profile of Ciclesonide, a Novel Corticosteroid for the Treatment of Asthma". The Journal of Pharmacology and Experimental Therapeutics, vol. 314, No. 2, 2005, pp. 568-574.
Couetil et al., "Inflammatory Airway Disease of Horses"., Journal of Veterinary Internal Medicine, vol. 21, 2007, pp. 356-361.
Dauvillier et al., "Effect of Long-Term Fluticasone Treatment on Immune Function in Horses with Heaves". Journal of Veterinary Internal Medicine, vol. 25, No. 3, pp. 549-557.
Derom et al., "Effects of inhaled ciclesonide and fluticasone propionate on cortisol secretion and airway responsiveness to adenosine 5' monophosphate in asthmatic patients." Pulmonary Pharmacology & Therapeutics, vol. 18, 2005, pp. 328-336.
Dietzel et al., "Ciclesonide: an On-Site-Activated Steroid". New Drugs for Asthma, Allergy and COPD. Progress in Respiratory Research, Basel, Karger, vol. 31, 2001, pp. 91-93.
Grahnén et al., "A dose-response study comparing supression of plasma cortisol influenced by fluticasone propionate from Diskhaler and budesonide from Turbuhaler"., European Journal of Clinical Pharmacology, vol. 52, 1997, pp. 261-267.
Holmes et al., "Horse carboxylesterases: Evidence for six CES1 and four families of CES genes on chromosome 3". Comparative Biochemistry and Physiology, Part D, vol. 4, 2009, pp. 54-65.
International Search Report and Written Opinion for PCT/EP2013/077266 dated Feb. 11, 2014.
Kutasi et al., "Diagnostic Approaches for the Assessment of Equine Chronic Pulmonary Disorders". Journal of Equine Veterinary Science, vol. 31, 2011, pp. 400-410.
Leclere et al., "Invited Review Series: Cutting Edge Technologies". Official Journal of the Asian Pacific Society of Respirology, Respirology, vol. 16, 2011, pp. 1027-1046.

(Continued)

*Primary Examiner* — Kathrien A Hartsfield
(74) *Attorney, Agent, or Firm* — Katrina Bergbauer

(57) ABSTRACT

The disclosure relates to the field of medicine, in particular to the field of veterinary medicine. The disclosure relates to a pharmaceutical (medicament) formulation of glucocorticoids, especially ciclesonide or a pharmaceutically acceptable derivative thereof.

12 Claims, No Drawings

(56) References Cited

OTHER PUBLICATIONS

Matera et al., "Innervation of Equine Airways". Pulmonary Pharmacology & Therapeutics, vol. 15, 2002, pp. 503-511.
MHRA (Public Assessment Report Mutual Recognition Procedure, 2008, pp. 1-61).
Mutch et al., "The role of esterases in the metabolism of ciclesonide to desisobutyryl-ciclesonide in human tissue". Biochemical Pharmacology, vol. 73, 2007, pp. 1657-1664.
ResearchGate (Asked Nov. 11, 2012 in the project Synthesis and characterization of polyazomethines and their optical, electrical and thermal properties, https://www.researchgate.net/post/How_will_i_make_0025_mole_hydrochloric_acid_solution) Tatiana P. Rogasevskaia (on Nov. 11, 2012).
Robinson et al., "Fluticasone Propionate Aerosol is More Effective for Prevention than Treatment of Recurrent Airway Obstruction". Journal of Veterinary Internal Medicine, vol. 23, 2009, pp. 1247-1253.
Robinson et al., "The airway response of horses with recurrent airway obstruction (heaves) to aerosol administration of ipratropium bromide". Equine Veterinary Journal, vol. 25, No. 4, 1993, pp. 299-303.
Robinson, N.E., "International Workshop on Equine Chronic Airway Disease. Michigan State University, Jun. 16-18, 2000". Equine Veterinary Journal vol. 33, No. 1, 2001, pp. 5-19.
Weinbrenner et al., "Circadian Rhythm of Serum Cortisol after Repeated Inhalation of the New Topical Steroid Ciclesonide". The Journal of linical Endocrinology & Metabolism, vol. 87, No. 5, pp. 2160-2163.

PHARMACEUTICAL FORMULATION COMPRISING CICLESONIDE

CROSS-REFERENCE TO RELATED APPLICATIONS

This application is a divisional of U.S. patent application Ser. No. 14/132,578, filed Dec. 18, 2013, which claims priority from European Patent Application No. 12199302.6, filed Dec. 21, 2012, and from European Patent Application No. 13190393.2, filed Oct. 25, 2013, the disclosures of which are all incorporated herein by reference in their entireties.

FIELD OF THE INVENTION

The invention relates to pharmaceutical formulations of the active substance ciclesonide, des-ciclesonide or a pharmaceutically acceptable derivative thereof, in particular for the field of veterinary medicine, more particularly for the field of equine medicine. The invention further relates to methods of preparing a pharmaceutical formulation comprising ciclesonide, des-ciclesonide or a pharmaceutically acceptable derivative thereof as well as an inhalation kit.

BACKGROUND INFORMATION

Due to the low water solubility of glucocorticoids, they are normally formulated as a solid for oral or inhalative application. Examples include orally administered tablets for prednisolone or a powder formulation for inhalation out of a dry powder inhaler (DPI) for budesonide. However, oral dosage forms of glucocorticoids have the disadvantage of frequent side effects especially after long-term use. Furthermore, the DPI inhaler type is acceptable for humans who can regulate their breathing to breath in the powder through the mouthpiece of an inhaler. Animals, however, cannot use such an inhaler since breathing cannot be coordinated to inhale a powder out of a DPI. For application to animals a pressurized multi-dose inhaler (pMDI) or an aqueous/ethanolic droplet inhaler (would be more suitable, as the liquid formulation in such inhalers is aerosolized by an energy source such as a refrigerant or a spring. It is possible to formulate a glucocorticoid for a pMDI or an aqueous/ethanolic droplet inhaler by producing a solution with a pharmaceutically acceptable co-solvent such as ethanol. Such a formulation for use in a pMDI is ALVESCO® for human use. The formulation of ALVESCO® is a solution of ciclesonide in a mixture of ethanol and refrigerant (hydrofluoroalkanes). However, the use of hydrofluoroalkanes as a refrigerant has disadvantages. Hydrofluoroalkanes have been found to degrade ozone in the atmosphere. Hence, it would be desirable to develop a formulation of a glucocorticoid that can be aerosolized but does not contain a hydrofluoroalkane.

BRIEF SUMMARY OF THE INVENTION

The present invention concerns a pharmaceutical (medicament) formulation comprising or containing as active substance one or more compounds of the formula I or II, preferably formula I, most preferably the R-enantiomer of formula I Formula I ciclesonide
(ciclesonide)

Formula II des-ciclesonide
(des-ciclesonide)

optionally in the form of the tautomers, enantiomers, mixtures of the enantiomers, racemates, solvates or hydrates thereof, at least one pharmacologically acceptable acid, optionally further pharmacologically acceptable excipients and/or solvents, whereby said formulation is preferably a liquid formulation containing as solvent ethanol or a mixture of water and ethanol, preferably an ethanolic solution for inhalation, preferably for veterinary use, preferably with an (equine) inhaler device. "Ethanolic" in this context refers to mixtures of ethanol and water as well as pure ethanol.

The invention concerns a pharmaceutical (medicament) formulation comprising or containing as active substance ciclesonide or a pharmaceutically acceptable salt thereof, preferably in the R-enantiomer form.

The pH value of an aqueous solution is defined as $-\log_{10}[H^+]$, where $[H^+]$ represents the activity of hydrogen ions which corresponds to the molar concentration in diluted solutions. The pH value of an ethanolic liquid formulation is not clearly defined. For this reason an "apparent" pH value for ethanolic solutions is defined in the present invention as $pH_{app}=-\log_{10}[H+]$. The value of $pH_{app}$ and the concentration of hydrogen ions, $[H^+]$, which reflects ionic strength, are inversely correlated. High $pH_{app}$ value ⇔ low value for $[H^+]$. In this text $pH_{app}$ refers to $-\log_{10}[H^+]$ and not to the value that is measured with a pH electrode such as for aqueous solutions.

For ethanolic formulations of ciclesonide it has been surprisingly found to be advantageous to set $pH_{app}$ in the range of 4.0 to 4.6. To identify an appropriate $pH_{app}$ in an ethanolic liquid formulation comprising ciclesonide is a challenge. On the one hand side the stability of ciclesonide is better at higher (more neutral) pH values. However, on the other hand, the pH should not be too high since at low $[H^+]$ values already small amounts of contaminants and decomposition products can cause a relatively large change in $pH_{app}$. Furthermore, the use of a buffer for inhalable formulations is undesirable due to the administration of the buffer constituents to the lungs and the possibility of the buffer constituents forming a residue in the inhaler which may affect the spray characteristics of the aerosol. Surprisingly, the $pH_{app}$ range of 4.0 to 4.6 allows for an ethanolic formulation of ciclesonide where ciclesonide is chemically stable and the $pH_{app}$ value remains stable. The addition of buffer is not necessary to create the advantageous formulation of the present invention.

According to a specific aspect of the present invention said formulation is a solution for inhalation. Equivalent terms are inhalable formulation or a formulation in the form of an inhalant. In another aspect of the present invention the formulation is in a liquid formulation, preferably an ethanolic formulation, which can be aerosolized to facilitate its inhalation. In a further aspect the liquid formulation is partially ethanolic and partially aqueous. In a further aspect of the present invention the liquid formulation comprises one or more of the solvents water, ethanol, and optionally additional excipients.

In a preferred aspect of the present invention the liquid formulation comprises a mixture of water and ethanol, e.g. 10% V/V aqueous and 90% V/V ethanolic.

In a further preferred aspect of the present invention the solvent of the liquid formulation comprises a mixture of ethanol and water, whereby the proportion of ethanol is in the range of 85-100% V/V, preferably 90-95% V/V. Preferably the proportion of ethanol is 90% V/V ethanol.

In a specific aspect of the present invention the formulation (solution for inhalation) of ciclesonide is as follows:

TABLE 1

| Ingredient | concentration [g/100 mL] |
|---|---|
| Ciclesonide | 3.0 |
| HCl 0.1 M [mL] | 0.0424 |
| [H⁺] [µmol/L] | 31.6 |
| $pH_{app}$ | 4.5 |
| Mass ethanol [g] | 68.8 |
| Mass water [g] | 11.5 |

For the solution listed in the Table 1 above the density was found to be 0.83 g/mL. More HCl is added than needed to achieve $-\log[H^+]=31.6$ µmol/L in demineralized water alone due to the buffering capacity of ciclesonide. It was found that this buffering capacity=-3.6 µmol/g ciclesonide, i.e. for 3.0 g of ciclesonide 10.8 µmol/L extra [H⁺] needs to be added to reach the value of 31.6 µmol/L. That means that the amount of HCl (0.1 M) needed for 100 mL to achieve $pH_{app}=4.5$ is 0.0316 mL+0.0108 mL=0.0424 mL.

In another specific aspect of the present invention the formulation (solution for inhalation) of ciclesonide is as follows:

TABLE 2

| Ingredient | Content |
|---|---|
| Ciclesonide | 0.7 – 3.1 g/100 mL |
| Hydrochloric acid | ad [H⁺] = $10^{-3.5}$ to $10^{-5}$ mol/L |
| 90% V/V ethanol/water | ad 100 mL | where the concentration of hydrogen ions [H⁺] can be measured, for example, by potentiometric titration.

A further aspect of the present invention is the application of the liquid formulation according to the present invention using an inhaler device, such as the RESPIMAT® inhaler or another inhaler using the RESPIMAT® aerosol-generating technology. The RESPIMAT® inhaler is disclosed for example in WO 97/12687, which is hereby incorporated by reference. Although this inhaler is presently marketed by Boehringer Ingelheim for human application as an aqueous droplet inhaler for use with aqueous solutions (SPIRIVA® RESPIMAT®, COMBIVENT® RESPIMAT®, BERODUAL® RESPIMAT®), this inhaler can advantageously be used to produce the inhalable aerosols/inhalants of ethanolic solutions according to the invention. The dose of active substance delivered ex RESPIMAT® inhaler can be calculated from:

the concentration of active substance in the liquid formulation (solution for inhalation) [µg/µL], the "delivered volume", defined as the volume of liquid expelled from the RESPIMAT® inhaler per actuation [µL]. The delivered volume ex RESPIMAT® inhaler has been found to be approximately 11 µL per actuation, according to the following formula:

$$\text{Dose [µg]}=\text{Concentration [µg/µL]}\cdot\text{Delivered Volume [µL]}$$

In a specific aspect of the present invention the pharmaceutical (medicament) formulation is administered via an inhaler device to a patient, preferably to an equine patient, most preferably to a horse. For the application in horses high doses and thus highly concentrated formulations are a prerequisite. Due to the low solubility of ciclesonide especially in water as well as the low chemical stability of ciclesonide at certain $pH_{app}$ values this is a challenge, especially in an ethanolic formulation.

Preferably said inhaler device comprises: (a) an aqueous/ethanolic droplet inhaler such as the RESPIMAT® inhaler or another inhaler using the RESPIMAT® aerosol-generating technology and (b) an adapter for equine use. In another specific aspect of the present invention the pharmaceutical (medicament) formulation is a partially/mainly ethanolic formulation and is administered via an (equine) inhaler device.

The invention further concerns a method for preparing a pharmaceutical (medicament) formulation according to the present invention characterized by the addition of a fixed amount of hydrochloride acid to the formulation in the production process. For formulations specified to have a certain pH value, according to the prior art the acid is normally slowly added (titrated) to the solution until the target pH value as measured by a pH electrode is reached. The process of the present invention is simpler since a fixed amount of a strongly dissociated acid (e.g. HCl) is added to the production vessel and no titration is necessary. The concentration of H⁺ ions [H⁺] can be checked, if necessary, using potentiometric titration.

The invention further concerns product produced by the above process as well as an inhalation kit consisting of or comprising a pharmaceutical (medicament) formulation according to the present invention, an (equine) inhaler device, preferably an aqueous/ethanolic droplet inhaler such as the RESPIMAT® inhaler or another inhaler using the RESPIMAT® aerosol-generating technology suitable for nebulizing this pharmaceutical (medicament) formulation, optionally an adapter for equine use, and optionally an instruction leaflet (enclosed label) or information and direction for use.

DETAILED DESCRIPTION OF THE INVENTION

Before describing the various aspects of the present invention it shall be noted that as used herein and in the appended claims, the singular forms "a", "an", and "the" include plural reference unless the context clearly dictates otherwise. Thus, for example, reference to "a preparation" includes a plurality of such preparations reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention. Terms not specifically defined herein should be given the meanings that would be given to them by one of skill in the art in light of the disclosure and the context. As used in the specification, however, unless specified to the contrary, the following terms have the meaning indicated and the following conventions are adhered to.

The term "ciclesonide" ((11β,16α)-16,17-[[(R)-Cyclohexylmethylene]bis(oxy)]-11-hydroxy-21-(2-methyl-1-oxopropoxy)pregna-1,4-diene-3,20-dione, $C_{32}H_{44}O_7$, $M_r$=540.7 g/mol) is well known in the art and means/describes a glucocorticoid used to treat asthma and allergic rhinitis in humans. It is marketed for application in humans under the brand name ALVESCO® for asthma and OMNARIS®/OMNIAIR® for hay fever in the US and Canada. Ciclesonide is a prodrug. It is transformed into the active metabolite C21-C21-desisobutyrylciclesonide (=desciclesonide) via hydrolysis by intracellular esterases in the lung. Ciclesonide is a non-halogenated glucocorticoid, which predominantly exists in the form of an R-Enantiomer.

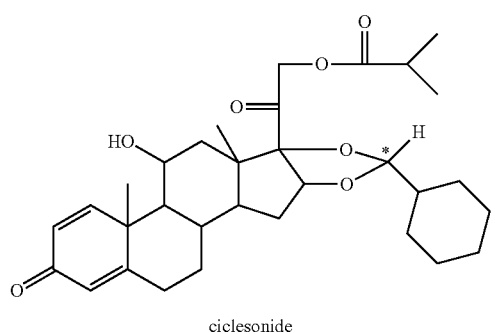

ciclesonide

Formula I

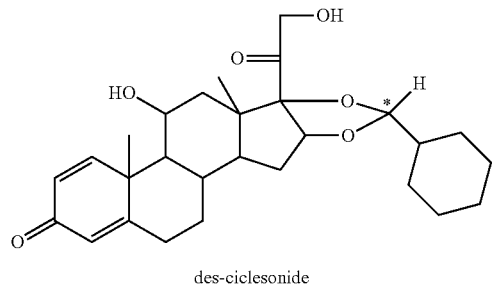

des-ciclesonide

Formula II

The prodrug nature of ciclesonide is an advantage for the pharmaceutical (medicament) formulation according to the present invention. It has been shown that the active metabolite (C21-C21-des-isobutyrylciclesonide) is generated only in the airways of humans or other mammals such as equines. The prodrug ciclesonide has to be activated by special enzymes in the airway tissues in order to generate C21-C21-des-isobutyrylciclesonide, which is the effective molecule.

Therefore, even if large amounts of ciclesonide are swallowed during aerosol treatment the prodrug nature of ciclesonide and the dependency on specific enzyme conversion in the lung for generation of the active compound C21-C21-des-isobutyrylciclesonide assures that the effect of ciclesonide is only related to the airways and not to the whole body of the horses. This is also referred to as a topical effect of ciclesonide. In contrast, the state of the art treatment with dexamethasone or other substances like fluticasone leads to a systemic exposure of the active metabolite, leading to an extensive side effect profile when administrating these other formulations of the prior art, for example DEXABENE® for dexamethasone dihydrogenphosphate disodium as an injection solution; or VIANI® DISCUS® for fluticasone propionate or PULMICORT® TURBOHALER® for budesonide) as powders for inhalation).

The term "dexamethasone" is well known in the art and means/describes a potent synthetic member of the glucocorticoid class of steroid drugs. It acts as an anti-inflammatory and immunosuppressant. When taken orally, it is 27 times more potent than the naturally occurring hormone cortisol and 7 times more potent than prednisone.

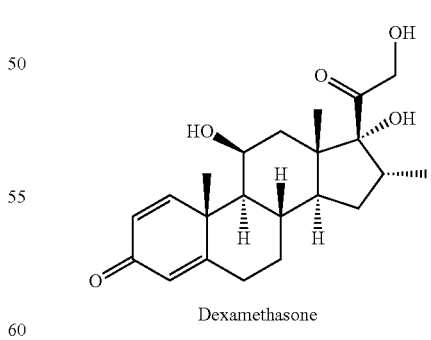

Dexamethasone

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in the case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can usually be readily prepared from the parent compounds using methods known in the art.

The term "equine" means of or belonging to the family Equidae, which includes the horses, asses, and zebras, preferably horses. In addition, the term "equine" encompasses also hybrids of members of the family Equidae (e.g. mules, hinnies, etc.).

The term "patient" or "subject" embraces mammals such as primates including humans. The term "patient" or "subject" as used herein relates specifically to equines such as horses, especially horses suffering from airway disease (particularly pulmonary disease).

The term "pharmaceutically acceptable derivative thereof" means but is not limited to pharmaceutically acceptable salts, derivatives, metabolites or pro-drugs of a drug. Derivatives as used herein include but are not limited to, any hydrate forms, solvates, isomers, enantiomers, racemates, racemic conglomerate and the like of the compound of choice. Suitable pharmaceutically acceptable salts are well known in the art and may be formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The term "pharmaceutical (medicament) formulation or solution" means non-pressurized metered-dose preparations for inhalation, which are solutions, suspensions or emulsions for use with inhalers that convert liquids into aerosols using single or multiple liquid jets, ultrasonic vibration or other methods. The volume of liquid to be converted into an aerosol is pre-metered or metered by the inhaler so that the dose delivered from the inhaler can be inhaled with 1 or more inspirations.

Administration

Suitable forms for "administration" are for example inhalation, parenteral or oral administration.

In the specific administration via the RESPIMAT® inhaler the content of the pharmaceutically effective ciclesonide should be in the range from 0.1 to 5% m/V, preferably 0.7 to 3.1% m/V or 1.0 to 3.1% m/V of the total composition, i.e. in amounts which are sufficient to achieve the dose range specified hereinafter.

When administered by inhalation ciclesonide may be given as an ethanolic solution or a solution containing a mixture of water and ethanol. Preferably, therefore, pharmaceutical formulations are characterized in that they comprise ciclesonide according to the preferred aspects above.

It is particularly preferred that ciclesonide is administered via inhalation/ex inhaler, preferably it is administered once or twice a day. Suitable formulations may be obtained, for example, by mixing ciclesonide with known excipients, for example water, pharmaceutically acceptable organic solvents such as mono- or polyfunctional alcohols (e.g. ethanol or glycerol). For a liquid formulation, additional excipients for example hydrochloric acid or citric acid to adjust the $[H^+]$ concentration may be added.

It is especially preferred that ciclesonide is administered by/via an aqueous/ethanolic droplet inhaler, for example the RESPIMAT® inhaler or another inhalation device using the RESPIMAT® aerosol-generating technology. Preferably, the pharmaceutical formulation comprising ciclesonide is administered once or twice a day. For this purpose, ciclesonide has to be made available in a liquid solution which is suitable for the inhaler.

Preferably the solvent in the liquid formulation (inhalation solution) comprises a mixture of water and ethanol, such as 10% V/V aqueous and 90% V/V ethanolic. In a further aspect of the present invention the solvent in the liquid formulation (inhalation solution) comprises a mixture of ≥85% V/V ethanol and ≤15% V/V water, such as 90% V/V ethanol and 10% V/V water.

In a further preferred aspect of the present invention the solvent in the liquid formulation (inhalation solution) comprises a mixture of ethanol and water, whereby the proportion of ethanol is in the range of 85-100% V/V, preferably 90-95% V/V. Preferably the proportion of ethanol is 90% V/V ethanol.

In a specific embodiment the formulation of ciclesonide is as follows:

TABLE 3

| Ingredient | Content |
| --- | --- |
| Ciclesonide | 0.7 – 3.1 g/100 mL |
| Hydrochloric acid | ad $[H^+]= 10^{-3.5}$ to $10^{-5}$ mol/L |
| 90% V/V ethanol/water | ad 100 mL | where the concentration of hydrogen ions $[H^+]$ can be measured, for example, by potentiometric titration.

A further aspect of the present invention is the application of the liquid formulation (inhalation solution) using the RESPIMAT® inhaler or another inhalation device based on the RESPIMAT® aerosol-generating technology. This inhaler is disclosed for example in WO 97/12687, which is hereby incorporated therein. This inhaler can advantageously be used to produce the inhalable aerosols according to the invention. The dose of active substance delivered ex RESPIMAT® inhaler can be calculated from:
 the concentration of active substance in the liquid formulation [µg/µL],
 the "delivered volume", defined as the volume of liquid expelled from the RESPIMAT® inhaler per actuation [4]. The delivered volume ex RESPIMAT® inhaler has been found to be approximately 11 µL per actuation, according to the following formula:

Dose [µg]=Concentration [µg/µL]·Delivered Volume [µL]

In a further aspect of the present invention the composition is administered via an (equine) inhaler device. The (equine) inhaler device preferably comprises/consists of the RESPIMAT® inhaler or another inhaler using the RESPIMAT® aerosol-generating technology, and other parts to adapt the inhaler to equine use. In a preferred aspect the composition is a partially ethanolic formulation and is administered via an (equine) inhaler device. The dose emitted via the (equine) inhaler device can be slightly lower than the dose ex RESPIMAT® inhaler.

The RESPIMAT® inhaler is one specific form of an aqueous/ethanolic droplet inhaler. Other aqueous/ethanolic droplet inhalers may be used.

The concentration of ciclesonide contained in the solution in the inhalation device ranges preferably from 0.7 to 5% m/V or 0.7 to 3.1% m/V.

The present invention concerns a pharmaceutical (medicament) formulation comprising/containing ciclesonide and/or des-ciclesonide as active substance, optionally in the form of the tautomers, enantiomers, mixtures of the enantiomers, racemates, solvates or hydrates thereof, at least one pharmacologically acceptable acid, optionally further pharmacologically acceptable excipients and/or solvents, whereby said formulation is an ethanolic solution or a solution containing a mixture of ethanol and water.

In a specific aspect of the present invention the proportion of ethanol in the (solvent consisting of a) mixture of ethanol and water is in the range of 85-100% V/V, preferably 90-95% V/V, most preferably 90% V/V. Further preferred is a proportion of ethanol ≥85% V/V ethanol, preferably ≥90% V/V ethanol.

In a specific aspect of the present invention said formulation is a solution for inhalation.

In a further specific aspect of the present invention the $-\log_{10}[H+]$ of said formulation is in the range of 4.0 to 4.6.

In a specific aspect of the present invention one (the) active substance is ciclesonide or a pharmaceutically acceptable salt thereof, preferably in the R-enantiomer form, preferably at a concentration of 0.1-5 g/100 mL, preferably 0.7-3.1 g/100 mL, most preferably at a concentration of 3 g/100 mL.

In another specific aspect of the present invention the pharmacologically acceptable excipient and/or solvent comprises (i) one or more of the following excipients and/or solvents selected from the group consisting of: water, a pharmaceutically acceptable organic solvent such as mono- or polyfunctional alcohol (e.g. glycerol or propanol), and (ii) optionally additional excipients and/or solvents.

In a further aspect of the present invention the pharmacologically acceptable acid is selected from the inorganic acids hydrochloric acid, phosphoric acid, hydrobromic acid, nitric acid and sulfuric acid or from the organic acids citric acid, tartaric acid, malic acid, maleic acid, succinic acid, fumaric acid, acetic acid, formic acid, propionic acid, sorbic acid, benzoic acid, methanesulfonic acid and benzenesulfonic acid, preferably the acid is hydrochloric acid.

In a preferred aspect of the present invention the pharmacologically acceptable acid is selected from the inorganic acids hydrochloric acid, phosphoric acid, and hydrobromic acid.

In a specific aspect of the present invention the formulation is administered via an (equine) inhaler device.

The invention further concerns a method of preparing a pharmaceutical (medicament) formulation according to the present invention comprising the following steps:
(a) Dissolving ciclesonide in a solvent comprising ethanol and water,
(b) Adding a fixed amount of acid, preferably hydrochloric acid (HCl), most preferably as a 0.1 or 1.0 molar solution. As a result thereof $-\log_{10}[H+]$ is in the preferable range of 4.0 to 4.6.

The invention further concerns a method of preparing a pharmaceutical (medicament) formulation according to the present invention comprising the following steps:
(a) Dissolving ciclesonide in a solvent comprising ethanol and water,
(b) Adding a fixed amount of acid, preferably hydrochloric acid (HCl), most preferably as a 0.1 or 1.0 molar solution, to reach a value of $-\log_{10}[H^+]=4.0$ to 4.6

In a specific aspect of the method according to the present invention the proportion of ethanol in the solvent of step (a) is in the range of 85-100% V/V, preferably 90-95% V/V, and most preferably the proportion of ethanol in the solvent of step (a) is 90% V/V ethanol.

Preferably ciclesonide is first dissolved in ethanol. This can be done by either adding ciclesonide to ethanol in a vessel or first weighing the appropriate amount of ciclesonide into the vessel and then adding ethanol. The amount of water needed to reach the target solvent composition is then added. Therefore, in a specific aspect of the present invention ciclesonide is first dissolved in ethanol and the amount of water needed to reach the target solvent composition is then added.

In a further specific aspect of the method according to the present invention the method comprises the additional steps:
(c) Mixing until a homogenous solution is formed,
(d) Optionally filtering the solution, preferably through one or more filters with a pore size of maximum 1.0 μm for at least one of the filters, most preferably of maximum 0.2 μm,
(e) Optionally filling the solution into containers.

Said containers are preferably appropriate for long-term storage and/or for use with the appropriate inhaler device (such as e.g. the RESPIMAT® inhaler or another inhaler using the RESPIMAT® aerosol-generating technology).

In a specific aspect of the present invention the inhaler device is an equine inhaler device, which preferably comprises/consists of the RESPIMAT® inhaler or another inhaler using the RESPIMAT® aerosol-generating technology, and other parts to adapt the inhaler to equine use.

The present invention further concerns a pharmaceutical (medicament) formulation comprising/containing ciclesonide as active substance obtainable/obtained/prepared by a method according to the present invention.

The present invention further concerns an inhalation kit comprising/consisting of a pharmaceutical (medicament) formulation according to the present invention, an (equine) inhaler device, preferably a pressurized metered dose inhaler or an aqueous/ethanolic droplet inhaler such as the RESPIMAT® inhaler or another inhaler using the RESPIMAT® aerosol-generating technology, suitable for nebulizing this pharmaceutical (medicament) formulation, optionally an adapter for equine use, and optionally an instruction leaflet (enclosed label) or information and direction for use.

EXAMPLES

The following examples serve to further illustrate the present invention; but the same should not be construed as a limitation of the scope of the invention disclosed herein.

Example 1 (Ciclesonide Formulations)

Ciclesonide monopreparation is formulated as a solution for inhalation as follows:

TABLE 4

| Ingredient | concentration [g/100 mL] |
| --- | --- |
| Ciclesonide | 3.0 |
| HCl 0,1 M [mL] | 0.0424 |
| c H$^+$ [µmol/L] | 31.6 |
| pH$_{app}$ | 4.5 |
| Mass Ethanol [g] | 68.8 |
| Mass Waster [g] | 11.5 |

The measured density of the above solution at 20° C. is 0.83 g/mL.

Another ciclesonide monopreparation is formulated as a solution for inhalation as follows:

TABLE 5

| Ingredient | Content |
| --- | --- |
| Ciclesonide | 0.7 – 3.1 g/100 mL |
| Hydrochloric acid | ad [H$^+$] = 10$^{-3.5}$ to 10$^{-5}$ mol/L |
| 90% V/V ethanol/water | ad 100 mL | where the concentration of hydrogen ions [H$^+$] can be measured, for example, by potentiometric titration.

Example 2 (Method for Preparing Ciclesonide Formulation)

A ciclesonide formulation (solution for inhalation) is prepared as follows:
1. 30 g Ciclesonide is weighed into a 2 L vessel
2. 687.5 g Ethanol (>99.9% purity) is added. The mixture is stirred until the ciclesonide dissolves and a homogeneous solution is formed.
3. 114.7 g Purified water is slowly added. The mixture is stirred until a homogeneous solution is formed.
4. 0.424 mL Hydrochloric acid (0.1M) is added. The mixture is stirred until a homogeneous solution is formed.
5. The resulting solution is filtered through a membrane filter with a 0.2 µm pore size using nitrogen pressure.
6. The filtered solution is filled into cartridges suitable for the RESPIMAT® inhaler.

The defined volume of HCl surprisingly shows a good correlation between pH$_{app}$ (target) and pH$_{app}$ (titration).

The invention claimed is:

1. A method of preparing a pharmaceutical formulation, comprising the following steps:
dissolving ciclesonide in a solvent comprising ethanol and water to form a solution; and
adding a fixed amount of a pharmaceutically acceptable acid at 0.1 or 1.0 molar to reach a value of –log$_{10}$[H+] in the range of 4.0 to 4.6 for the solution wherein the acid comprises hydrochloric acid (HCl).

2. The method of claim 1, wherein a proportion of ethanol in the solvent is in a range of 85-100% V/V.

3. The method of claim 1, wherein a proportion of ethanol in the solvent is in a range of 90-95% V/V.

4. The method of claim 1, wherein a proportion of ethanol in the solvent is 90% V/V ethanol.

5. The method of claim 1, wherein ciclesonide is first dissolved in ethanol and an amount of water needed to reach a target solvent composition for the solution is then added.

6. The method of claim 1, further comprising:
mixing until a homogeneous solution is formed.

7. The method of claim 1, further comprising:
filtering the solution through one or more filters with a pore size of maximum 1.0 µm for at least one of the filters.

8. The method of claim 7, wherein said pore size maximum for at least one of the filters is 0.2 µm.

9. The method of claim 1, further comprising:
filling the solution into containers appropriate for long term storage and for use with an inhaler.

10. The method of claim 1, wherein ciclesonide is dissolved in the solvent in a sufficient amount such that the formulation includes ciclesonide at a concentration of 0.7 g/100 mL to 5 g/100 mL.

11. The method of claim 1, wherein ciclesonide is dissolved in the solvent in a sufficient amount such that the formulation includes ciclesonide at a concentration of 0.7 g/100 mL to 3.1 g/100 mL.

12. The method of claim 1, wherein ciclesonide is dissolved in the solvent in a sufficient amount such that the formulation includes ciclesonide at a concentration of 3 g/100 mL.

* * * * *